(12) United States Patent
He et al.

(10) Patent No.: US 11,420,072 B2
(45) Date of Patent: Aug. 23, 2022

(54) METHOD FOR INCREASING BLOOD FLOW AND METABOLIC RATE OF EYE FUNDUS

(71) Applicants: ZHONGSHAN OPHTHALMIC CENTER, SUN YAT-SEN UNIVERSITY, Guangdong (CN); SUZHOU XUANJIA OPTICS AND ELECTRONICS TECHNOLOGY CO. LTD., Jiangsu (CN)

(72) Inventors: Mingguang He, Guangzhou (CN); Zhaoyun Cao, Guangzhou (CN); Zhuoting Zhu, Guangzhou (CN)

(73) Assignees: ZHONGSHAN OPHTHALMIC CENTER, SUN YAT-SEN UNIVERSITY, Yuexiu District Guangzhou (CN); SUZHOU XUANJIA OPTICS AND ELECTRONICS TECHNOLOGY CO. LTD., New District Suzhou (CN)

( * ) Notice: Subject to any disclaimer, the term of this patent is extended or adjusted under 35 U.S.C. 154(b) by 0 days.

(21) Appl. No.: 17/345,150

(22) Filed: Jun. 11, 2021

(65) Prior Publication Data

US 2021/0402205 A1 Dec. 30, 2021

Related U.S. Application Data

(63) Continuation of application No. PCT/CN2020/098413, filed on Jun. 28, 2020.

(30) Foreign Application Priority Data

Jun. 6, 2019 (CN) .......................... 201910490186.6

(51) Int. Cl.
*A61N 5/06* (2006.01)
*A61N 5/067* (2006.01)
*A61F 9/008* (2006.01)

(52) U.S. Cl.
CPC .. *A61N 5/0613* (2013.01); *A61F 2009/00863* (2013.01); *A61N 5/067* (2021.08); *A61N 2005/0651* (2013.01); *A61N 2005/0659* (2013.01); *A61N 2005/0663* (2013.01)

(58) Field of Classification Search
CPC ...... A61N 5/06; A61N 5/0613; A61N 5/0618; A61N 5/062; A61N 5/0622; A61N 2005/0627; A61N 2005/0643; A61N 2005/0648; A61N 2005/065; A61N 2005/0651; A61N 2005/0654; A61N 2005/0658; A61N 2005/0659; A61N 2005/0662; A61N 2005/0663; A61N 5/067; A61F 9/007; A61F 9/00727; A61F 2009/00861; A61F 2009/00863; A61F 2009/00874

USPC .......................... 607/88, 89, 96; 606/3, 4, 6
See application file for complete search history.

(56) References Cited

U.S. PATENT DOCUMENTS

| 5,161,526 A | 11/1992 | Hellwing et al. |
| 2005/0159793 A1 | 7/2005 | Streeter |
| 2007/0016074 A1* | 1/2007 | Abreu ................ A61B 5/14539 600/475 |
| 2011/0202114 A1 | 8/2011 | Kessel et al. |
| 2013/0027662 A1 | 1/2013 | Matsuoka |
| 2015/0173949 A1* | 6/2015 | Humayun ............. A61F 9/0079 601/2 |
| 2018/0193187 A1 | 7/2018 | Rozsa |
| 2018/0200532 A1 | 7/2018 | Luttrull et al. |
| 2018/0345034 A1* | 12/2018 | Butzloff ............... A61N 5/0613 |

FOREIGN PATENT DOCUMENTS

| CN | 1216002 | 5/1999 |
| CN | 102894953 | 1/2013 |
| CN | 109069294 | 12/2018 |
| CN | 109620137 | 4/2019 |
| CN | 110237432 | 9/2019 |
| RU | 2032432 | 4/1995 |
| WO | 2016-040534 | 3/2016 |
| WO | WO2017/192168 | 11/2017 |
| WO | 2019-0999068 | 5/2019 |

OTHER PUBLICATIONS

International Search Report for PCT/CN2020/098413 dated Aug. 26, 2020, 2 pages.
Examination Report No. 2 as received in Australian patent application No. 2020233703, dated Mar. 16, 2022, 5, pages.
Ivayla I. Geneva, "Photobiomodulation for the treatment of retinal diseases: a review", Int. J. Ophthalmol, vol. 9 , No. 1, Jan. 18, 2016, pp. 145-152.
Ivandic, et al., "Low-Level Laser Therapy Improves Vision in a Patient with Retinitis Pigmentosa", Photomedicine and Laser Surgery, vol. 32, No. 3, (2014), © Mary Ann Liebert, Inc, pp. 181-184.

* cited by examiner

*Primary Examiner* — Ahmed M Farah
(74) *Attorney, Agent, or Firm* — Oblon, McClelland, Maier & Neustadt, L.L.P.

(57) ABSTRACT

A method for increasing the blood flow and metabolic rate of the eye fundus by (1) irradiating the eye fundus through the pupil by using red light or near-infrared light in a certain wavelength range, a certain energy density range and a certain irradiation time range; (2) once irradiation is complete, repeating the irradiating at intervals of a certain time range, using red light or near-infrared light in the same wavelength range and the same energy density range to irradiate the eye fundus through the pupil.

7 Claims, No Drawings

METHOD FOR INCREASING BLOOD FLOW AND METABOLIC RATE OF EYE FUNDUS

This application is a continuation of PCT/CN2020098413, filed Jun. 28, 2020, which claims the benefit of CN application 201910490186.6(CN), filed Jun. 6, 2019, the contents of bot are incorporated herein by reference.

TECHNICAL FIELD

The present invention relates to a method for increasing the blood flow and metabolic rate of the eye fundus for preventing, delaying, inhibiting, or even reversing eye diseases.

BACKGROUND

Laser was first used in the irradiation for retinal detachment in ophthalmology in 1962. For half a century, laser has been widely used in the diagnosis and treatment of ophthalmology, from confocal laser scanning microscopy, optical coherence tomography (OCT) and other ophthalmic auxiliary examinations based on laser, to laser photocoagulation, transpupillary thermotherapy (TTT) and photodynamic therapy (PDT) and other methods of treating eye diseases based on laser irradiation. The main mechanism of laser irradiation for treating eye disease is thermal effect. For example, the underlying mechanism of transscleral cyclophotocoagulation irradiation for refractory glaucoma and retinal photocoagulation irradiation for diabetic retinopathy (DR) is photocoagulation effect, which increases the tissue temperature by 60-100° C. in a short time; and the underlying mechanism of the recently emerging TTT irradiation for wet age-related macular degeneration (AMD) is photothermal effect, that is, increasing temperature by 42-60° C. While PDT destroys neovascularization in the wet AMD by stimulating exogenous photosensitizer with laser to produce actively oxidative substances and induce the photo dynamic effect. However, it is worth noting that conventional high-intensity laser irradiation for treating eye diseases also causes damage to normal tissues, thereby resulting in a series of complications such as retinal fibrosis.

Photobiomodulation does not depend on the thermal effect (only increasing temperature of tissue by 0.1-0.5° C.), but uses the photochemical transformation potential of low-intensity red light and near-infrared light to cause a photochemical reaction of target tissue, including improving the activity of cytochrome C oxidase, modifying the gene expression to regulate the mitochondrial respiratory chain, and increasing the biological activity of nitric oxide, etc. It is worth noting that in recent years, light-emitting diode (LED) has become an important light source of low-intensity red light and near-infrared phototherapy in addition to laser due to its long service life, low price, high safety and comparable photochemical effect with laser.

As an innovative and non-invasive therapy, low-intensity red light and near-infrared light therapy have been initially applied to wound healing, nerve pain, peripheral nerve injury, stroke and other systemic diseases, and achieved certain efficacy, and such novel phototherapy has also provided new ideas and methods of therapy for various vision-threatening eye diseases. Russian patents No. RU2265464, RU2267339 and RU2274477 issued to И.П. Шурыгина, et al. use a low-intensity near-infrared laser irradiator to irradiate the occipital head, neck and carotid sinus to increase the orbital blood circulation for preventing and delaying myopia and amblyopia in children (RU2265464; RU2267339; RU2274477). Chinese Patent No. CN101822872A issued to Chao Qu, et al. discloses a method of irradiating the traditional Chinese medicine acupuncture points in ocular regions with low-intensity near-infrared light for treating chronic mitochondrial lesions, injury related diseases and nervous diseases. Ivandic et al. use low-intensity red light (at a wavelength of 780 nm) through conjunctiva and sclera to effectively improve the visual function and corresponding symptoms of AMD, adult amblyopia and retinitis pigmentosa (RP). Tang et al. use low-intensity red light (at a wavelength of 670 nm) to irradiate the closed eyelids, so as to effectively improve the retinal non-foveal edema in diabetic patients.

It is worth noting that the irradiating sites of the aforesaid low-density red light and near-infrared light are body surface, acupuncture points, or conjunctiva, while no method of directly irradiating the eye fundus has been reported. Fundus is the functional area for generating visual signals, has important ocular structures such as retina, choroid and sclera, and also has important cellular structures like retinal photoreceptor cells, choroidal vessels, scleral fibroblasts and fibroblasts. Low-intensity red light and near-infrared light can penetrate through transparent tissues such as cornea, lens and vitreous without pathological damage.

SUMMARY OF THE INVENTION

To address the aforesaid defects in the prior art, the present invention provides a method for increasing the blood flow and metabolic rate of the eye fundus, which aims to improve the repair effect of ocular tissue damages by increasing the blood flow and metabolic rate of the eye fundus tissue, including, but not limited to remodeling of scleral fibroblasts and repairing of visual function cells, so as to achieve the effects of preventing, delaying, inhibiting, or even reversing eye diseases.

To address the aforesaid technical problem, the technical solution utilized by the present invention includes:

A method for increasing the blood flow and metabolic rate of the eye fundus, including the following steps: (1) irradiating the eye fundus through the pupil by using the red light or near-infrared light of a certain wavelength range, a certain energy density range, and for a certain range of irradiation time; (2) once irradiation is complete, repeating the foregoing step at intervals of a certain time range, using the red light or the near-infrared light of the same wavelength range, and the same energy density range to irradiate the eye fundus through the pupil.

Preferably, in Step (2), a manner of repeating for multiple times is utilized. Preferably, in Step (2), said repeating the foregoing step means that the eye fundus is irradiated through the pupil twice to three times per day, and the irradiations are performed at an interval of at least two hours, the number of days required is at least 30 days.

Preferably, low-intensity red light or near-infrared light is used as said red light or near-infrared light.

Preferably, said low-density red light or near-infrared light has a light wavelength in a range of 630-1000 nm.

Preferably, said low-density red light or near-infrared light has a light wavelength in a range of 650 or 810 nm.

Preferably, said low-density red light or near-infrared light has an energy density in a range of 0.5-25 J/cm$^2$.

Preferably, said low-density red light or near-infrared light has an energy density in a range of 0.5-15 J/cm$^2$.

Preferably, the light source of said low-intensity red light or near-infrared light includes, but is not limited to, laser diodes (LDs), light-emitting diodes (LEDs), or bulbs.

Preferably, GaAlAs LDs, GaAsPa LDs, or AlGALP LDs are used as said laser diodes.

Preferably, in Step (1), said irradiation time is in a range of 150 s to 210 s.

Preferably, in Step (1), said irradiation time is 180 s.

The beneficial effects of the present invention include: direct irradiation of the eye fundus with low-intensity red light and near-infrared light through the pupil will more effectively and safely play the photophysical and photochemical effects, improve the metabolic rate and blood circulation of the eye fundus, improve the repair effect of ocular tissue damage, such as, increasing the blood circulation and oxygen supply of retina, choroid and sclera in myopic patients, and in turn promote the remodeling of fibroblasts to prevent, delay, inhibit and even reverse myopia. The present invention can also act on the visual functional cells, increase the metabolism and blood circulation of the visual functional cells, and effectively reduce the damage and improve the repair of the functional cells, so as to prevent, delay, inhibit and even reverse the eye diseases.

DETAILED DESCRIPTION OF THE EMBODIMENTS

A method for increasing the blood flow and metabolic rate of the eye fundus, including the following steps: (1) irradiating the eye fundus through the pupil by using the red light or near-infrared light of a certain wavelength range, a certain energy density range, and for a certain range of irradiation time; (2) once irradiation is complete, repeating the foregoing step at intervals of a certain time range, using the red light or the near-infrared light of the same wavelength range, and the same energy density range to irradiate the eye fundus through the pupil. Said repeating the foregoing step means that the eye fundus is irradiated through the pupil twice to three times per day, and the irradiations are performed at an interval of at least two hours, the number of days required is at least 30 days. Of those, low-intensity red light or near-infrared light is used as said red light or near-infrared light, said low-density red light or near-infrared light having a light wavelength in a range of 630-1000 nm. Said low-density red light or near-infrared light has preferably a light wavelength in a range of 650 nm or 810 nm. In Step (1), said irradiation time is in a range of 150 s to 210 s, preferably 180 s. Said low-density red light or near-infrared light has an energy density in a range of 0.5-25 J/cm$^2$. Preferably, the energy density is in a range of 0.5-15 J/cm$^2$. The light source of the low-intensity red light or near-infrared light includes, but is not limited to, laser diodes (LDs), light-emitting diodes (LEDs), or bulbs. Preferably, GaAlAs LDs, GaAsPa LDs, or AlGALP LDs are used as said laser diodes.

Working Example 1: A patient with myopia, male, 7 years old, the axial length of right eye: 23.73 mm, spherical equivalent: −4.875 D; the axial length of left eye: 23.62 mm, spherical equivalent: −4.5 D. The method for increasing the blood flow and metabolic rate of the eye fundus used in this example has achieved the effects of delaying, inhibiting, or even reversing myopia. A low-density red light was emitted by a diode at a wavelength of 650±10 nm. The laser power at a distance of 100 mm from the light source is 1.07~1.42 mW; the spot at the observation port is 10 mm±2 mm, and the energy density is in a range of 13-25 J/cm$^2$. The aforesaid method of repeatedly irradiating the eye fundus with a low-density red light to delay, inhibit, or even reverse the myopia specially includes the following steps: A. irradiating the eye fundus through the pupil with the above low-intensity red light with the duration of each irradiation of 180 s; B. irradiating the eye fundus twice per day at an interval of at least 2 hours. The low-density red light irradiation lasted for 3 months. The axial length of the right eye is shortened by 0.16 mm, and the spherical equivalent diopter is reduced by 0.625 D. The axial length of left eye is shortened by 0.08 mm, and the spherical equivalent diopter is reduced by 0.25 D.

Clinical experiments: the aforesaid method was performed in a total of 84 myopic children aged from 6 to 23, wherein the ratio of male to female was 1.08:1, and the duration of irradiation was 6 months. The annual change of the axial length for the right eye (one of the most important parameters for myopia progression) is −0.14±0.42 mm/y, and the annual change of the axial length of the left eye is −0.23±0.40 mm/y, indicating that the repeatedly irradiation of the eye fundus with low-density red light through the pupil can inhibit or even reverse myopia.

Working mechanism: a method of repeatedly irradiating the eye fundus with low-intensity red light and near-infrared light through the pupil is provided. Its underlying mechanism is the photophysical and photochemical effects produced by low-intensity red light and near-infrared light, improving the metabolic rate and blood circulation of ocular tissue, and increasing the repair effect of ocular tissue damage, including, but not limited to the remodeling of scleral fibroblasts and the repair of visual function cells, so as to achieve the effects of preventing, delaying, inhibiting or even reversing eye diseases, including but not limited to myopia, normal tension glaucoma, age-related maculopathy, diabetic retinopathy and retinitis pigmentosa.

The foregoing is the preferred embodiments of the present invention, and certainly it is not for the purpose of limiting the scope of the claims of the present invention. It is noted that persons skilled in the art can make modifications or equivalent substitutions on the technical solutions of the present invention without departing from the protection scope of the technical solutions of the present invention.

The invention claimed is:

1. A method for increasing the blood flow and metabolic rate of an eye fundus in a subject in need thereof, the method comprising (1) irradiating the eye fundus through the pupil with red light or near-infrared light having a light wavelength in a range of 630-1000 nm and an energy density in a range of 0.5-25 J/cm$^2$, and the irradiation time is in a range of 150 s to 210 s; (2) repeating the irradiating of the eye fundus through the pupil two to three times per day with the red light or the near-infrared light of the same wavelength range and the same energy density range to irradiate the eye fundus through the pupil.

2. The method for increasing the blood flow and metabolic rate of the eye fundus according to claim 1, wherein the irradiations are performed at an interval of at least two hours and for at least 30 days.

3. The method for increasing the blood flow and metabolic rate of the eye fundus according to claim 1, wherein the red light or near-infrared light is provided by at least one of a laser diode (LD), a light-emitting diode (LED), or a bulb.

4. The method for increasing the blood flow and metabolic rate of the eye fundus according to claim 3, wherein the low-intensity red light or near-infrared light is provided by a laser diode (LD) that is at least one of GaAlAs LD, GaAsPa LD, or AlGALP LD.

5. The method for increasing the blood flow and metabolic rate of the eye fundus according to claim 1, wherein the red light or near-infrared light has an energy density of 0.5 to 15 J/cm².

6. The method for increasing the blood flow and metabolic rate of the eye fundus according to claim 1, wherein the red light or near-infrared light has a light wavelength of 650 nm or 810 nm.

7. The method for increasing the blood flow and metabolic rate of the eye fundus according to claim 1, wherein the irradiating in (1) is for a time of 180 s.

* * * * *